United States Patent
Shaw et al.

(10) Patent No.: US 11,219,580 B2
(45) Date of Patent: Jan. 11, 2022

(54) ORAL COMPOSITION (71) Applicant: Andalay Technologies Limited, Exeter (GB)

(72) Inventors: Andrew Mark Shaw, Exeter (GB); Tim Holdway, Exeter (GB); Alasdair Dow, Exeter (GB)

(73) Assignee: ANDALAY TECHNOLOGIES LIMITED, Exeter (GB)

(*) Notice: Subject to any disclaimer, the term of this patent is extended or adjusted under 35 U.S.C. 154(b) by 0 days.

(21) Appl. No.: 16/096,865

(22) PCT Filed: Apr. 28, 2017

(86) PCT No.: PCT/GB2017/051211
§ 371 (c)(1),
(2) Date: Oct. 26, 2018

(87) PCT Pub. No.: WO2017/187198
PCT Pub. Date: Nov. 2, 2017

(65) Prior Publication Data
US 2019/0133892 A1  May 9, 2019

(30) Foreign Application Priority Data
Apr. 29, 2016  (GB) .................. 1607518

(51) Int. Cl.
A61K 8/11 (2006.01)
A61K 8/03 (2006.01)
A61Q 11/00 (2006.01)
A61K 8/04 (2006.01)
A61K 8/73 (2006.01)
A61K 8/65 (2006.01)
A23G 3/36 (2006.01)

(52) U.S. Cl.
CPC .............. A61K 8/042 (2013.01); A23G 3/36 (2013.01); A61K 8/03 (2013.01); A61K 8/11 (2013.01); A61K 8/65 (2013.01); A61K 8/73 (2013.01); A61K 8/731 (2013.01); A61Q 11/00 (2013.01); A61K 2800/56 (2013.01)

(58) Field of Classification Search
CPC .. A61K 2300/00; A61K 8/042; A61K 9/0053; A61K 9/006; A61K 2800/5424; A61K 45/06; A61K 2800/56; A61K 2800/92; A61K 8/03; A61K 8/11; A61Q 11/00
See application file for complete search history.

(56) References Cited

U.S. PATENT DOCUMENTS

| 4,994,276 A | 2/1991 | Baichwal | |
| 5,270,031 A * | 12/1993 | Lim | A61K 8/27 424/49 |
| 5,437,856 A | 8/1995 | Lukacovic | |
| 5,900,230 A | 5/1999 | Cutler | |
| 6,485,771 B1 * | 11/2002 | Somerville | A23C 9/1544 426/519 |
| 6,685,978 B1 * | 2/2004 | Hauksson | A23B 4/0235 426/573 |
| 2002/0081267 A1 | 6/2002 | Barabolak | |
| 2004/0121061 A1 | 6/2004 | Uchida | |
| 2004/0180110 A1 * | 9/2004 | Mistry | A23G 3/36 426/3 |
| 2004/0258733 A1 | 12/2004 | Maxwell | |
| 2006/0024248 A1 * | 2/2006 | Spengler | A61Q 11/00 424/49 |
| 2007/0292372 A1 * | 12/2007 | Clarot | A61K 8/731 424/58 |
| 2008/0081023 A1 * | 4/2008 | Deckner | A61K 8/731 424/49 |
| 2009/0214445 A1 * | 8/2009 | Boghani | A23G 4/20 424/48 |
| 2009/0318388 A1 * | 12/2009 | Spasojevic | A61K 31/555 514/90 |
| 2010/0237281 A1 * | 9/2010 | Jensen | A61K 8/84 252/186.42 |
| 2011/0305738 A1 * | 12/2011 | Ladizinsky | A61K 8/02 424/401 |
| 2013/0189202 A1 * | 7/2013 | Tsugane | A23G 4/068 424/58 |
| 2015/0272159 A1 * | 10/2015 | Pontzer | A23G 1/205 426/103 |
| 2016/0136192 A1 * | 5/2016 | Vazhappilly | A61K 9/0056 514/77 |

(Continued)

FOREIGN PATENT DOCUMENTS

CN  101534823  9/2009
JP  2003081794 A  3/2003

(Continued)

OTHER PUBLICATIONS

Ottenbrite, "Frontiers in biomedical polymer applications" vol. 1. CRC Press, 1998.
Durig, et al. "Guar-based monolithic matrix systems: effect of ionizable and non-ionizable substances and excipients on gel dynamics and release kinetics." Journal of controlled release 80.1-3 (2002): 45-56.

(Continued)

Primary Examiner — Tracy Liu
(74) Attorney, Agent, or Firm — Tarolli, Sundheim, Covell & Tummino LLP (57) ABSTRACT The present invention provides a mouthwash composition comprising a heterogeneous gel, wherein said heterogeneous gel comprises at least two gelling agents and two or more active ingredients, and wherein the composition provides the differential release of the active ingredients over a period of time.

20 Claims, 6 Drawing Sheets (56) References Cited

U.S. PATENT DOCUMENTS

2017/0326068 A1* 11/2017 Morimoto .............. A61K 47/12

FOREIGN PATENT DOCUMENTS

| | | |
|---|---|---|
| JP | 2004300119 A | 10/2004 |
| JP | 2012056870 | 3/2012 |
| JP | 2012193150 A | 10/2012 |
| JP | 2013193969 A | 9/2013 |
| WO | 9000387 A1 | 1/1990 |
| WO | 9622701 A1 | 8/1996 |
| WO | 03002056 A2 | 1/2003 |
| WO | 2006081867 A1 | 8/2006 |
| WO | 2014059679 A1 | 4/2014 |
| WO | 2014156505 A1 | 10/2014 |
| WO | 2015039277 A1 | 3/2015 |
| WO | WO-2016129289 A1 * 8/2016 ............. A61K 47/12 |

OTHER PUBLICATIONS

Lowe, et al. "Effect of hydrophobicity of a drug on its release from hydrogels with different topological structures." Journal of applied polymer science 73.6 (1999): 1031-1039.

Dixit, et al. "Oral strip technology: overview and future potential." Journal of controlled release 139.2 (2009): 94-107.

* cited by examiner

Figure 1: Composition A

Figure 2: Composition B

Figure 3: Composition C

Figure 4: Composition D

Figure 5: Composition E

Figure 6: Composition F

ORAL COMPOSITION

The present invention provides a mouthwash composition, a process for its preparation, a package comprising a single dose or unit of the mouthwash composition, and the use of the mouthwash composition to deliver active ingredients.

A conventional mouthwash is a liquid which is swilled around the mouth and sometimes gargled before being discarded. A conventional mouthwash is employed primarily to clean the mouth and freshen the breath. Conventional mouthwashes are not convenient for use away from the home, for example, when at work or eating out, since they are not intended to be consumed. Many conventional mouthwashes also have a very strong unpleasant taste or even provide a burning sensation when retained within the mouth for an extended period of time. For this reason, it is believed that less than half of the UK population uses mouthwash. Many mouthwashes are also not suitable for children.

The present invention, which relates to a mouthwash composition in the form of a gel, has been devised with these issues in mind.

It is known in the art to employ gels in oral hygiene products such as toothpastes and mouthwashes—see, for example, WO 2014/059679, WO 90/00387, WO 2014/156505, JP 2012193150, JP 2004300119 and JP 2003081794. WO 2014/059679 discloses a method for making a toothpaste composition, which comprises the following steps:

(i) Dispersing guar gum into a first aqueous medium comprising sorbitol to produce a first gellant dispersion;
(ii) Dispersing at least one cellulose polymer into a second aqueous medium to produce a second gellant dispersion;
(iii) Combining the first and second gellant dispersions to produce a third gellant dispersion; and
(iv) Mixing the third gellant dispersion with a plurality of toothpaste components (e.g. abrasives etc.) to produce a toothpaste composition.

There is, however, no disclosure in any of these documents of a mouthwash composition which provides a differential release of its active ingredients over a period of time. Thus, there is still a need for further and improved mouthwash compositions.

According to a first aspect, the present invention provides a mouthwash composition comprising a heterogeneous gel, wherein said heterogeneous gel comprises at least two gelling agents and two or more active ingredients, and wherein the composition provides differential release of the active ingredients over a period of time. Preferably the mouthwash composition of the present invention sequentially releases an effective amount of the two or more active ingredients over a period of time. This means that at least two of the active ingredients in the composition reach an effective amount or concentration in situ after different periods of time have elapsed after placing the mouthwash composition in a mouth.

As used herein, a "mouthwash composition" is a composition which is intended to be held temporarily in the mouth and is suitable for cleaning, freshening breath and/or the delivery one or more active components to the mouth. It will thus be understood that the term "mouthwash" does not imply a liquid composition. As the mouthwash composition of the present invention is not intended to be used in combination with a toothbrush, it will also be understood that the term "mouthwash" does not include toothpaste.

The mouthwash of the invention provides a different experience for the consumer since it is in the form of a gel. The gel can be squeezed though the teeth and therefore encourages the consumer to retain the product in the mouth for longer. The gel consistency thus enables the mouthwash to provide release of an active ingredient over a longer period of time than is typically achieved with conventional liquid mouthwashes. Moreover the mouthwash composition of the present invention is preferably edible. Unlike conventional mouthwashes and toothpastes, which are mainly spat out of the mouth after use, the mouthwash composition of the present invention is intended to be swallowed. Advantageously this makes the mouthwash composition of the present invention easy to use when the user is away from home and also by a range of different types of people, including children.

In some embodiments the composition is capable of forming a film on a buccal surface, such as the surface of a tooth (i.e. a biocomposite), gum, cheeks and/or tongue. In one embodiment the composition provides a film which remains on the surface for a duration of at least 3 minutes, at least 5 minutes, at least 8 minutes or at least 10 minutes. In some embodiments the film may be completely lost after 10 minutes.

The film may be formed rapidly after the mouthwash is placed in the mouth. The film may provide an interface between the rest of the gel in the buccal cavity and the surfaces of the mouth, in particular the teeth. Without being bound by theory, it is believed that as molecules are released from the bulk of the mouthwash composition, they are then adsorbed into the film before passing onto the mouth or tooth surface. The film thus allows molecules to be adsorbed from the contents of the buccal cavity. The delivery of active ingredients to the film from the bulk of the composition, and the loss from the film into the tooth or other mouth surface, are balanced to provide an effective half-life of the composition. The extended residence time of the film on the surfaces of the mouth, as compared to conventional liquid mouthwashes, provides enhanced exposure to active ingredients present in the composition.

The mouthwash composition of the present invention preferably comprises: (i) a first gel comprising a surfactant, a first gelling agent and optionally one or more active ingredients; and (ii) a second gel comprising a second gelling agent and one or more active ingredients. Preferably the affinity of the surfactant for the first gel is lower than the affinity of at least one of the one or more active ingredients for the first gel and/or the second gel.

Preferably, when the mouthwash composition is placed in a mouth, the surfactant is readily released from the first gel into the buccal cavity. Preferably therefore the surfactant concentration reaches an effective amount in the buccal cavity prior to at least one of the other one or more active ingredients achieving an effective amount thereof. Particularly preferably the composition sequentially releases an effective amount of the surfactant and then an effective amount of at least one of the one or more active ingredients over a period of time. By the term "effective amount" is meant the amount or concentration that is necessary for an ingredient to have its desired effect. This term may also be described as an effective dose. Thus the "effective amount" of any given active ingredient will be different. For example, the "effective amount" of surfactant is likely to be different to the "effective amount" of sweetening agent. The preferred mouthwash compositions of the present invention sequentially release an effective amount of surfactant prior to at least one of the other one or more active ingredients. This means that the amount or concentration of surfactant reaches the level required to facilitate the formation of a film of the composition on the teeth and remove oils and fats from the teeth, prior to the amount or concentration of at least one of the other one or more active ingredients reaching its effective amount.

The mouthwash composition of the present invention releases an effective amount of surfactant in a relatively short period of time after the composition is placed in a mouth. Advantageously the surfactant facilitates the formation of the above-mentioned film on the surfaces of the mouth, and in particular the teeth. The teeth tend to be covered with fats and oils after the consumption of food and the hydrophobic part of the surfactant readily interacts therewith. This helps to remove these compounds from the teeth surfaces prior to their contact with other active ingredients of the composition, such as NaF, which otherwise might not reach the teeth surfaces. Furthermore the surfactant also helps to ensure that there is homogeneity between the mouthwash composition and the saliva.

Preferably the mouthwash composition of the present invention also releases an effective amount of pH-buffering agent in a relatively short period of time after the composition is placed in a mouth. Like the surfactant, the pH-buffering agent, helps to prepare the tooth surface for formation of a film and for treatment by other active ingredients. Preferably therefore the composition sequentially releases an effective amount of the surfactant and an effective amount of a pH-buffering agent and then an effective amount of at least one of the one or more active ingredients over a period of time.

As mentioned above the mouthwash composition of the present invention preferably forms a film upon contact with a buccal surface. It is an advantage of the present invention that the film increases the residence time of the one or more active ingredients on the buccal surface. By "residence time" is meant the time for which the given active ingredient is in contact with a buccal surface. With a conventional liquid mouthwash composition, the residence time of the active ingredients present therein is generally the same as the time for which the mouthwash composition is retained in the mouth before being spat out. With the mouthwash composition of the invention, which is in the form of a gel that preferably forms a film upon contact with a buccal surface, the residence time is significantly increased because after the majority of the composition has been swallowed, the film remains on the surface of the teeth and retains the one or more active ingredients therein, where they are in contact with the buccal surface.

The mouthwash composition of the present invention preferably is retained in the mouth for up to 180 seconds, e.g. 30 to 180 seconds. More preferably the mouthwash composition is retained in the mouth for 60 to 180 seconds or 120 to 180 seconds. By the phrase "retained in the mouth" is meant the duration of time for which substantially the entirety of the mouthwash composition is present in the mouth of a user, i.e. the time between placing the mouthwash composition in the mouth and removal of the mouthwash composition from the mouth. Preferably the mouthwash composition is swallowed at the end of this time.

Preferably the mouthwash composition of the present invention has a longer residence time in the mouth than the time for which it is retained in the mouth. Preferably the mouthwash composition has a residence time of greater than 180 s. Preferably the mouthwash composition provides release of the active ingredients over a period of time of greater than 180 s. This may be achieved by the mouthwash composition of the present invention because, as described above, it forms a film on the buccal surface. Active ingredients may be advantageously retained in this film after the majority of the composition is swallowed and provide further release of active ingredients.

In some embodiments the composition is edible, i.e. the composition is intended to be consumed in its entirety. An edible composition is particularly convenient for use at work, when travelling or when eating out. An edible composition is also suitable for children.

The composition comprises a heterogeneous gel. By "heterogeneous" it will be understood that the composition comprises two or more gels which are blended together. One or more of the gels may be hydrogels.

The present invention therefore also provides a mouthwash composition comprising a heterogeneous gel, wherein said heterogeneous gel comprises: (i) a first gel comprising a surfactant, a first gelling agent and optionally one or more active ingredients; and (ii) a second gel comprising a second gelling agent and one or more active ingredients, wherein the affinity of said surfactant for said first gel is lower than the affinity of at least one of said one or more active ingredients for said first gel and/or said second gel.

The heterogeneous gel contains at least two gelling agents. In some embodiments, the gelling agents are selected from the group consisting of xanthan gum, gellan gum, gum arabic, guar gum, locust bean gum, methylcellulose, carboxymethyl cellulose, gelatin, carrageenan, agar and pectin. The at least two gelling agents may be different (such as methylcellulose and gelatin), or they may be different forms of the same gelling agent (such as gellan gum low acyl (e.g. type F) and gellan gum high acyl (e.g. type LT100)). The present inventors have found that these gelling agents provide a suitable texture in the mouth.

In some embodiments the heterogeneous gel comprises methylcellulose and xanthan gum. Preferably the first gel, additionally comprising a surfactant, comprises xanthan gum. Preferably the second gel comprises methylcellulose.

In some embodiments the heterogeneous gel comprises gellan gum, preferably low-acyl gellan gum and high-acyl gellan gum, and optionally gelatin. Preferably the first gel, additionally comprising a surfactant, comprises high-acyl gellan gum. Preferably the second gel comprises low-acyl gellan gum.

Preferably the mouthwash composition of the present invention further comprises a sweetening agent. Preferably the composition sequentially releases: (i) an effective amount of the surfactant and an effective amount of the sweetening agent; and (ii) an effective amount of the one or more active ingredients. When a pH-buffering agent is additionally present, the composition preferably sequentially releases (i) an effective amount of the surfactant, an effective amount of the pH-buffering agent and an effective amount of the sweetening agent; and then (ii) an effective amount of the one or more active ingredients. Preferably the sweetening agent is released in effective amount relatively quickly after the mouthwash composition is placed in the mouth so that it can mask the taste of other unpleasant tasting active ingredients.

The at least one or more active ingredient may be selected from the group consisting of humectants (e.g. sorbitol), flavourants, colourings or pigments, antiseptics, antimicrobials (including antibiotics, antivirals and antifungals), anti-caries agents (e.g. zinc citrate, zinc gluconate), anticalculus agents (i.e. tartar control agents), oral cleaning agents, abrasive agents, desensitizing agents (e.g. inorganic ions such as $K^+$), strengthening agents (e.g. fluoride ion sources such as sodium fluoride), bleaching or whitening agents, sweeteners (e.g. polyols), medicaments, pH-modifying agents, surfactants, cooling agents, herbal agents, vitamins and combinations thereof. Preferably the at least one or more active ingredient is selected from the group consisting of humectants (e.g. sorbitol), flavourants, colourings or pigments, antiseptics, antimicrobials (including antibiotics, antivirals and antifungals), anticaries agents (e.g. zinc citrate, zinc gluconate), anticalculus agents (i.e. tartar control agents), oral cleaning agents, abrasive agents, desensitizing agents (e.g. inorganic ions such as $K^+$), strengthening agents (e.g. fluoride ion sources such as sodium fluoride), bleaching or whitening agents, medicaments, cooling agents, herbal agents, vitamins and combinations thereof. It will be understood that a single ingredient may have more than one effect.

Suitable flavourants include peppermint oil, menthol, *eucalyptus* oil, vanillin, sage, thymol, marjoram, parsley oil, spearmint oil, cinnamon oil, oil of wintergreen (methyl salicylate), clove oil, bay oil, anise oil, citrus oils, and fruit oils and essences including those derived from lemon, orange, lime, grapefruit, apricot, banana, grape, apple, strawberry, cherry, and pineapple.

In some embodiments, the flavorant comprises peppermint oil, menthol, eucalyptus, and/or thymol.

In some preferred embodiments the composition comprises a surfactant. A surfactant provides surface wetting properties and therefore helps the film adhere to the surface of the tooth, gum, cheek and/or tongue.

Suitable surfactants include sorbitan monolaurate, sodium lauryl sulfate, sodium coconut monoglyceride sulfonate, sodium lauryl sarcosinate, sodium lauryl isoethionate, sodium laureth carboxylate, sodium dodecyl benzenesulfonate, poloxamers, polyoxyethylene sorbitan esters, fatty alcohol ethoxylates, alkylphenol ethoxylates, tertiary amine oxides, tertiary phosphine oxides, and dialkyl sulfoxides. In one embodiment the surfactant is sorbitan monolaurate.

In one series of embodiments the composition comprises at least 0.01 wt %, at least 0.05 wt % or at least 0.1 wt % surfactant.

In some embodiments the composition comprises a sweetener. The sweetener may be selected from dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, mannitol, sorbitol, xylitol, maltitol, isomalt, and combinations thereof. In one embodiment the sweetener comprises xylitol. Xylitol is known to be beneficial for the teeth.

In one series of embodiments the composition comprises at least 3 wt %, at least 5 wt % or at least 10 wt % sweetener. In one series of embodiments the composition comprises no more than 50 wt %, no more than 30 wt % or no more than 20 wt % sweetener.

In some embodiments the composition comprises a pH modifying agent. This may be employed to provide pH buffering at the tooth, cheek and/or tongue surface to neutral pH. Modifying the pH at the surface helps to prepare the surface to facilitate the delivery of other active ingredients to the surface.

In some embodiments, the composition is capable of providing the differential release of active ingredients over a period of time.

By "differential release" it will be understood that the active ingredients are released at different rates. In some embodiments, a first active ingredient may be released entirely, followed by the release of a second active ingredient. However, it is not necessary that the active ingredients are released consecutively, and the release of different active ingredients may overlap. For example, in some embodiments a first active ingredient may be released at a rapid rate initially and then at a slower rate, while the rate of release of a second active ingredient increases gradually, or remains substantially constant. The release of one or more of the active ingredients may be delayed, such that the ingredient is not released straightaway on placing the composition into the mouth. The composition therefore enables the release of different active ingredients in sequence.

In some embodiments, the composition may be formulated such that the active ingredients are released in two more phases. The phases may be sequential. For example, in a first phase film formation, surface wetting and/or pH buffering may occur. In a second phase an antimicrobial agent may be released. In a third phase inorganic ions such as $K^+$ for desensitization may be released. In some embodiments the phases may overlap.

The sequence of release of different active ingredients may conveniently be tailored in accordance with a desired effect (e.g. dental hygiene). A preferred mouthwash composition of the present invention provides the differential release, and more preferably sequential release of an effective amount, of at least a surfactant, a sweetening agent and at least one of the one or more active ingredients, preferably flavourants, antiseptics, antimicrobials, anticaries agents, anticalculus agents, oral cleaning agents, abrasive agents, desensitizing agents, strengthening agents, bleaching or whitening agents, medicaments, cooling agents, herbal agents, vitamins and combinations thereof. Preferably the mouthwash composition of the invention sequentially releases an effective amount of a surfactant and an effective amount of a sweetening agent and then an effective amount of one or more active ingredients selected from flavourants, antiseptics, antimicrobials, anticares agents, anticalculus agents, oral cleaning agents, abrasive agents, desensitizing agents, strengthening agents, bleaching or whitening agents, medicaments, cooling agents, herbal agents, vitamins and combinations thereof.

The composition may be capable of providing the release of one or more of the active ingredients over a period of time of at least 2 minutes, at least 3 minutes, at least 5 minutes, at least 8 minutes, at least 10 minutes or at least 15 minutes.

For example, the composition may be formulated to provide film formation, surface wetting and/or pH buffering initially, so as to prepare the surface of the tooth, gum, cheek and/or tongue. The composition may then release one or more further active ingredients to the prepared surface, such as antimicrobials and/or desensitizers.

The differential or sequential release of different active ingredients can be achieved in numerous ways, many of which will be known to those skilled in the art. For example, the release of an active ingredient may be controlled by the affinity of the active ingredient for one or both of the gels forming the heterogeneous gel. The higher the affinity of the active ingredient for the gel, the slower the release. The release of an active ingredient may also be controlled by the concentration of the active ingredient in the gel, by the viscosity of the gel(s), by the overall structure of the heterogeneous gel and so on. The skilled man can readily determine the release rate of any active ingredient from a given gel in the presence of water by standard test procedures wherein the gel is placed in water and the change in concentration of the active ingredient in water is measured over time.

An active ingredient may be associated with one or more gels of the heterogeneous gel. In some embodiments, and as described above, the composition may comprise one or more active ingredients associated with a first gel, and one or more active ingredients associated with a second gel. The active ingredient(s) associated with the first gel may be same or different to those associated with the second gel. By "associated with", it will be appreciated that the active ingredient(s) is suspended or dispersed within the gel matrix. The active ingredient(s) may have an affinity for the gel which can vary in strength, for example from being physically trapped within the gel matrix to being weakly bound to the gel e.g. by hydrogen bonding. As the gel is broken down by the effects of mastication, temperature, pH, salivary amylase, salinity and/or hydration, the active ingredient(s) is released.

In some embodiments, the two or more gels differ from each other in their hydrophilicity. For example, the composition may comprise a first gel and a second gel, wherein the first hydrogel is more hydrophilic than the second gel.

In some embodiments, the (or one of the) active agent(s) is constituted by or comprises a pro-drug. The pro-drug may be activated in situ in the mouth by, for example, the action of salivary amylase or temperature. In some embodiments, the composition may further comprise an activating agent (e.g. a separating agent or enzyme) for activating the pro-drug. The pro-drug is then activated once the activating agent is released from the gel. The composition may be formulated such that the activating agent is released after the pro-drug, or release of the activating agent is initiated after release of the pro-drug is initiated. This enables controlled activation of the pro-drug.

The mouthwash composition of the invention may be similar in texture to a sports gel. The composition may have a viscosity of from 1000 to 2000 or from 1200 to 1800 c.p. at 20° C. A sports-gel style mouthwash is better for moving around the mouth during mastication. The temptation to swallow is low, with the dissolution into the mouth being very effective. A jelly or sweet-like mouthwash may be particularly appealing for children.

In some embodiments, the mouthwash composition has a viscosity of no greater than 500,000, no greater than 250,000, no greater than 100,000, no greater than 50,000, no greater than 30,000, no greater than 20,000, no greater than 10,000 or no greater than 5000 c.p. at 20° C., In some embodiments, the mouthwash composition has a viscosity of from 2000 to 500,000, from 5,000 to 300,000, from 10,000 to 100,000 or from 25,000 to 70,000 c.p. at 20° C.

In some embodiments, the mouthwash composition is similar in texture to a jelly. The composition may have a viscosity of from 300,000 to 500,000 c.p. at 20° C.

In some embodiments, the mouthwash composition may be substantially solid, for example it may take the form of a chewable jelly sweet or gum or lozenge. The composition may have a mass of from 5 to 15 g, or from 8 to 12 g.

In some embodiments the mouthwash composition is provided as a single dose or unit which has a mass appropriate for a single, comfortable mouthful. The mass may be typically 12 g for adults and 8 g for children. The mouthwash composition may conveniently be packaged in individually-wrapped doses. Thus according to a further aspect of the invention there is provided a package comprising a single dose or unit of mouthwash composition as hereinbefore described.

According to a further aspect of the invention there is provided the non-medical use of a mouthwash composition as hereinbefore described to clean teeth and/or freshen breath. Such use is a cosmetic use, i.e. cosmetic use of a mouthwash composition as hereinbefore described to clean teeth and/or freshen breath.

In some embodiments, the composition is formulated such that the concentration of each active ingredient achieved locally within the film that is formed on the buccal surfaces exceeds the Effective Dose_50. The composition may also be formulated such that excessive consumption does not result in the Lethal Dose_50 of any active ingredient being exceeded. For example, the composition may be formulated such that 400×12 g units must be consumed per day in order to exceed the Lethal Dose_50 for each active ingredient.

In some embodiments the composition comprises an antimicrobial agent. A mouthwash composition comprising an antimicrobial agent may be particularly suited for use by intubated patients, who often suffer from bacterial or fungal infections, such as an oral infection and/or pneumonia.

Thus, in a further aspect the invention provides a mouthwash composition for use in the treatment of infection in a patient, wherein the mouthwash composition comprises a heterogeneous gel comprising at least one antimicrobial agent.

The patient may be intubated.

The composition may be capable of providing controlled release of the antimicrobial agent over a period of time, for example at least 5 minutes, at least 10 minutes or at least 15 minutes.

The antimicrobial agent may be an antibiotic. The antibiotic may be a broad spectrum antibiotic. The antibiotic may be suitable for treating infection by Gram negative bacteria. Suitable antibiotics include polymixin E and tobramycin. In some embodiments, the antimicrobial agent is an antifungal (e.g. amphotericin B). In some embodiments, the composition comprises a combination of antimicrobial agents. The antimicrobial agent may be present in the composition in an amount of from 0.5 to 5%, or from 1 to 3%, e.g. 2% w/v.

In some embodiments, the mouthwash composition has at least some of the following properties:
- film-forming on a buccal surface (or on the surface of an implant, such as an orthodontic implant or intubation tube);
- controlled and differential delivery of active ingredients over time;
- pH buffering;
- surface wetting properties;
- edible;
- storage stable.

According to a further aspect of the invention there is provided a method of preparing a mouthwash composition in the form of a gel as hereinbefore described, the method comprising:
- providing a first component;
- providing a second component; and
- mixing the first and second components together to provide a heterogeneous mixture, wherein the first and/or second components comprises at least one active ingredient.

In some embodiments the first and/or second component is in the form of a gel prior to mixing. Both the first and second components may be in the form of a gel prior to mixing. The gels are thus blended but not homogenized, thereby retaining different gel domains in the final composition which can provide differential release of active ingredients.

The first and/or second component in the form of a gel may be provided by dissolving a gelling agent in water with heating to form a solution and allowing the solution to cool so as to form a gel prior to mixing. One or more active ingredients may be added to the solution prior to cooling. The gel may be set partially or completely before mixing.

In some embodiments, the first and/or second component is in the form of a solution comprising a gelling agent. It will be appreciated that if the first and second components are mixed thoroughly while in the form of a solution, a homogeneous mixture will form. A heterogeneous mixture may be provided by incomplete mixing of the first and second components. In some embodiments, the first and/or second components may be cooled prior to mixing.

The method may further comprise a step of allowing the heterogeneous mixture to set so as to form the gel. The mixture may be allowed to set by cooling. In some embodiments, the method may additionally comprise adding a further gelling agent to the heterogeneous mixture prior to allowing the mixture to set.

A solution may be heated so as to dissolve the gelling agent. For example, a solution may be prepared by heating an amount of a liquid, such as water, and dissolving the gelling agent in the liquid.

In some embodiments, a first component in the form of a solution may be mixed with a second component which is in the form of a gel. The mixture may then be allowed to set, e.g. by cooling. This will form a heterogeneous gel which is a suspension of one component in the other.

In some embodiments, the method further comprises adding a colouring and/or a flavouring to the heterogeneous mixture.

In some embodiments the method further comprises coating or encapsulating the heterogeneous mixture. The heterogeneous mixture may be encapsulated by injecting the heterogeneous mixture into a hollow shell, such as a hollow sweet or lozenge. The heterogeneous mixture may be formed into soft gel capsules using, for example, a rotary die encapsulation process.

In some embodiments the method further comprises dispensing the mixture into a mould prior to allowing the mixture to set. Dispensing the mixture into a mould tray comprising multiple cavities enables individual doses of the mouthwash to be prepared.

It will be understood that the statements made above in relation to the first aspect of the invention may be applicable to any of the other aspects of the invention, and vice versa, as appropriate.

The invention will now be described by way of example and with reference to the following drawings in which.

EXAMPLES

Methodology

Three different types of mouthwash were prepared: (1) a sports gel type having relatively low viscosity, (2) a jelly and (3) a lozenge.

1A. Protocol for the Production of 600 mL of Sports-Gel Style Mouthwash
  i. Heat 120 mL of water to 70° C.
  ii. Add the following components to the water to provide solution A:
    a. 30,000 mg of xylitol
    b. 9,000 mg of potassium nitrate
    c. 7.5 mg of sodium fluoride
    d. 3.6 mL of colouring—this depends on the intensity of colour desired. Couple with colouring in iv.
    e. 7,500 mg of methylcellulose
  iii. Remove solution A from heat and add 120 mL of cold water, setting aside to cool.
  iv. Heat 360 mL of water to 100° C.
  v. Add the following components to the water to provide solution B:
    a. 1,500 µL of sorbitan monolaurate
    b. 720 µL of peppermint oil—this depends on the strength of the gel desired.
    c. 150 mg of menthol
    d. 72 µL of eucalyptol
    e. 18 mg of thymol
    f. 3.6 mL of food colouring—this depends on the intensity of colour desired
    g. 1,500 mg of xanthan
  vi. Remove solution B from heat and set to the side to cool.
  vii. Once both are cooled, mix together crudely and quantitatively add colouring and peppermint oil to adjust taste.

This sports gel-style mouthwash requires gums to ensure a timely release of each of the active ingredients. Methylcellulose and xanthan gums were chosen for this application.

1B. Protocol for the Production of 600 mL of Sports-Gel Style Mouthwash
  i. Heat 300 mL of water to 100° C. to provide solution A.
  ii. Heat 300 mL of water to 100° C. to provide solution B.
  iii. Soak 21.88 g of leaf gelatine leaves in water at room temperature.
  iv. Add the following components to solution A:
    a. 50 g xylitol
    b. 15 g potassium nitrate
    c. 12.5 mg sodium fluoride
    d. 2.5 g Gellan type F
  v. Add the following components to solution B:
    a. 2.5 mL sorbitan monolaurate
    b. 250 mg menthol
    c. 30 mg thymol
    d. 2.5 g Gellan LT100
    e. 35.5 mL of glycerol f. 7.2 mL of peppermint oil—this depends on the strength of the gel desired g. 720 µL of eucalyptol vi. Mix solution A and solution B together, maintaining the temperature at 100° C. The solution will appear opaque and gelatinous.

vii. Remove the leaf gelatine from the cold water and add this to the mixture of solutions A and B formed in step vi. The leaf gelatine should fully dissolve within 2-5 minutes.

viii. Once the mixture has a uniform appearance, quantitatively add food colouring.

ix. Pour the mixture into moulds and leave to cool.

This sports-gel style mouthwash employs Gellans to allow the timely release of the active ingredients. Gellan Type F (low acyl) and Gellan Type LT100 (high acyl) were chosen.

2. Protocol for the Production of 600 g of a Jelly-Style Mouthwash i. Heat 300 mL of water to 100° C.

ii. Add the following components to the water to provide solution A:
   a. 50,000 mg of xylitol
   b. 15,000 mg of potassium nitrate
   c. 12.5 mg of sodium fluoride
   d. 6 mL of colouring—this depends on the intensity of colour desired. Couple with colouring in iv.
   e. 1,000 mg of Gellan Type F iii. Remove solution A from heat.

iv. Heat another 300 mL of water to 100° C.

v. Add the following components to the water to provide solution B:
   a. 2,500 µL of sorbitan monolaurate
   b. 1.2 mL of peppermint oil—this depends on the strength desired
   c. 250 mg of menthol
   d. 120 µL of eucalyptol
   e. 30 mg of thymol
   f. 6 mL of food colouring—this depends on the intensity of colour desired
   g. 1,000 mg of Gellan Type LT100 vi. Mix solution A with solution B and immediately add 5000 mg vegetarian gelling agent. Stir until dissolved, pour into moulds and leave to cool.

The jelly style mouthwash employs Gellans to allow the timely release of the active ingredients. Gellan Type F (low acyl) and Gellan Type LT100 (high acyl) were chosen.

3. Protocol for the Production of 600 mL of Wine Gum Style Mouthwash:

i. Heat 120 mL of water to 70° C.

ii. Add the following components to the water to provide solution A:
   a. 30,000 mg of xylitol
   b. 9,000 mg of potassium nitrate
   c. 7.5 mg of sodium fluoride
   d. 3.6 mL of colouring—this depends on the intensity of colour desired. Couple with colouring in iv.
   e. 7,500 mg of methylcellulose iii. Remove solution A from heat and add 120 mL of cold water, setting aside to cool.

iv. Heat 360 mL of water to 100° C. Add the following components to the water to provide solution B:
   a. 1,500 µL of sorbitan monolaurate
   b. 720 µL of peppermint oil—this depends on the strength of the gel desired
   c. 150 mg of menthol
   d. 72 µL of eucalyptol
   e. 18 mg of thymol
   f. 3.6 mL of food colouring—this depends on the intensity of colour desired
   g. 1,500 mg of xanthan h. Remove solution B from heat and set to the side to cool.

i. Once both solutions are cooled, mix together crudely and quantitatively add colouring and peppermint oil to adjust taste.

j. Hollow out the centre of 600 vegetarian wine gums sufficiently to allow for the injection of 1 g of the mixture. Inject the mixture.

k. Melt the unmarked side of the wine gums sufficiently to achieve a sticky surface. Attach to the injected wine gums prepared in vii and hold together for 60 seconds to ensure binding of the two wine gums is complete.

The wine gum style formulation involves the injection of 1 mL of the sports gel formulation into a vegetarian wine gum.

Example Formulations

TABLE 1

Active Ingredient Formulation of a 12 g sample of sports gel-style mouthwash

| Component | Formulation per dose/mg | $LD_{50}$ rat | Mass fraction (% w/w) |
| --- | --- | --- | --- |
| Xylitol | 600 | 16,500 mg/kg | 5.0% |
| Potassium nitrate | 180 | 3,750 mg/kg | 1.5% |
| Sorbitan monolaurate | 30 µL | 36,700 µL/kg | 0.25% |
| Peppermint oil | 24 µL | 2,426 mg/kg | 0.18% |
| Menthol | 3 | 3,300 mg/kg | 0.025% |
| Eucalyptol | 1.44 µL | 2,480 mg/kg | 0.011% |
| Thymol | 0.36 | 980 mg/kg | 0.0030% |
| Sodium fluoride | 0.15 | 52 mg/kg | 0.0013% |

TABLE 2

Active Ingredient Formulation of a 4.4 g sample of jelly-style mouthwash

| Component | Formulation per dose/mg | $LD_{50}$ rat | Mass fraction (% w/w) |
| --- | --- | --- | --- |
| Xylitol | 366.67 | 16,500 mg/kg | 8.33% |
| Potassium nitrate | 110 | 3,750 mg/kg | 2.50% |
| Sorbitan monolaurate | 18.33 µL | 36,700 µL/kg | 0.43% |
| Peppermint oil | 52.8 µL | 2,426 mg/kg | 0.39% |
| Menthol | 1.83 | 3,300 mg/kg | 0.042% |
| Eucalyptol | 5.28 µL | 2,480 mg/kg | 0.041% |
| Thymol | 0.22 | 980 mg/kg | 0.0050% |
| Sodium fluoride | 0.092 | 52 mg/kg | 0.0021% |

The concentration of peppermint oil and eucalyptol can be increased to reflect different sensitivities to peppermint.

TABLE 3

Formulation of peppermint oil for three different strengths of sports gel-style mouthwash

| Formulation | Formulation per dose/mg | $LD_{50}$ rat | Mass fraction (% w/w) |
|---|---|---|---|
| '100' | 14.4 μL | 2,426 mg/kg | 0.11% |
| '300' | 24 μL | 2,426 mg/kg | 0.18% |
| '500' | 43.2 μL | 2,426 mg/kg | 0.32% |

TABLE 4

Formulation of eucalyptol for three different strengths of sports gel-style mouthwash

| Formulation | Formulation per dose/mg | $LD_{50}$ rat | Mass fraction (% w/w) |
|---|---|---|---|
| '100' | 1.44 μL | 2,480 mg/kg | 0.011% |
| '300' | 2.4 μL | 2,480 mg/kg | 0.018% |
| '500' | 4.32 μL | 2,480 mg/kg | 0.033% |

TABLE 5

Formulation of peppermint oil for three different strengths of jelly-style mouthwash

| Component | Formulation per dose/mg | $LD_{50}$ rat | Mass fraction (% w/w) |
|---|---|---|---|
| '100' | 17.6 μL | 2,426 mg/kg | 0.35% |
| '300' | 52.8 μL | 2,426 mg/kg | 0.39% |
| '500' | 80.7 μL | 2,426 mg/kg | 1.65% |

TABLE 6

Formulation of eucalyptol for three different strengths of jelly-style mouthwash

| Formulation | Formulation per dose/mg | $LD_{50}$ rat | Mass fraction (% w/w) |
|---|---|---|---|
| '100' | 1.76 μL | 2,480 mg/kg | 0.037% |
| '300' | 5.28 μL | 2,480 mg/kg | 0.11% |
| '500' | 8.07 μL | 2,480 mg/kg | 0.17% |

TABLE 7

Gel Formulation for a sports gel-style mouthwash 12 g sample

| Component | Formulation per dose/mg | $LD_{50}$ rat | Mass fraction (% w/w) |
|---|---|---|---|
| Methylcellulose | 150 | NA (too high) | 2.0% |
| Xanthan | 30 | NA (too high) | 0.20% |
| Water | 10754 μL | 90,000 mg/kg | 89.63% |
| Colouring | 144 μL | NA | 1.20% |

TABLE 8

Gel formulation for a jelly-style mouthwash based on 4.4 g sample

| Component | Formulation per dose/mg | $LD_{50}$ rat | Mass fraction (% w/w) |
|---|---|---|---|
| Gellan Type F (low acyl) (Supplier Cream Supplies) | 18.33 | NA (too high) | 0.42% |
| Gellan Type LT100 (high acyl) (Supplier Cream Supplies) | 18.33 | NA (too high) | 0.42% |
| Water | 3116 μL | 90,000 mg/kg | 70.82% |
| Food colouring | 240 μL | NA | 5.45% |
| Platinum Grade Leaf Gelatin (Dr. Oetker) | 160.45 | NA | 3.60% |
| Glycerine (Dr. Oetker) | 260 μL | 12,600 mg/kg | 7.45% |

Dissolution Tests

Dissolution Test 1

Six different mouthwash compositions (A-F) were prepared and formulated into 12 g units. Each composition contained a number of different active ingredients having a range of different molecular weights.

A single preparation unit (12 g) was added to a water-based solution maintained at 30° C. and stirred. Samples were removed from the supernatant at intervals forming a time course measurement. Each sample was then subject to electrospray ionization analysis with no preceding separation column. The variation in composition was then observed over time and plotted. The temporal dissolution profile of classes of molecules, grouped by mass (0-100, 100-200 etc.), is shown in FIGS. 1 to 6.

The dissolution profiles show that molecules of different mass class are released at different rates. Some have a single early phase which may be associated with surfactant and surfactant-soluble molecules; others show a later dissolution profile associated with the different phases in the gel formulation. Some mass classes show two peaks with contributions from different phases as they disperse into solution. It is believed that the composition of the film on the surface of the teeth, gum and cheek shows similar temporal dissolution behaviour as the composition of different mass classes in the mouth changes during the consumption of the gel. The film will be transient on the surface, further changing the composition time profile of the components. Any surface properties such as channels for the adsorption of K+ or oppositely charged surface groups and gel-phase species will be attracted and form an enhanced concentration-time profile. Similarly charged surface and gel-phase species will form depleted concentration-time profiles.

Dissolution Test 2

A sports-gel style mouthwash was prepared according to protocol 1B described above. In order to measure the release of the active ingredients from the mouthwash, it was necessary to recreate the mastication conditions of the mouth. The following protocol was employed for this purpose:

i. Whilst stirring with a 3.5 cm magnetic stirrer set at the "7" rotation setting, heat 100 mL of water to 37° C. in a beaker.

ii. Aspirate 1 mL of solution using a pipette to obtain a standard sample.

iii. Add 10 g of the sports-gel style mouthwash prepared according to protocol 1B to the heated water.

Aspirate 1 mL of the resultant solution at time intervals of t=10, 20, 40, 60, 90, 120, 150, 180, 210, 240, 270, 300, 360 and 600 seconds, ensuring that the samples are taken from the outermost rim of the beaker.

Prior to mass spectrometry analysis, the samples and standards obtained were diluted 1 part in 10 in acetonitrile (ACN). All concentrations given below for the calibration are of these diluted solutions.

All samples and calibration standards were injected in the following order: triplicate injections of full calibration standards from low to high concentration, triplicate injection of acetonitrile blank, triplicate injection of sample series B in timeline sequence (each with a single blank in between), single injection of full calibration standards from low to high concentration, triplicate injection of blank acetonitrile, triplicate injection of sample series B in timeline sequence (each with a single blank in between). The reason for the second, shorter, series of calibration standards was to determine if there was any significant decrease in sensitivity (indicated by decrease in peak area) during the batch.

The QTOF-UHPLC analysis was conducted using a MaXis HD quadrupole electrospray time-of-flight (ESI-QTOF) mass spectrometer (Bruker Daltonik GmbH, Bremen, Germany) operated in ESI positive-ion MS mode. The QTOF was coupled to an Ultimate 3000 UHPLC (Thermo Fisher Scientific, California, USA). The capillary voltage was set to 4500 V, nebulising gas at 2 bar, drying gas at 10 L/min at 200° C. The TOF scan range was from 50-750 mass-to-charge ratio (m/z). For effective transmission of ions the ion energy was set to 1.0 eV with the collision energy for TOF MS acquisition at 2.0 eV. Liquid chromatography was performed using a Kinetex 1.7 μM, 2.1×100 mm HILIC column (Phenomenex) with a flow rate of 0.4 mL/min at 30° C. and an injection volume of 10 μL. Mobile phases A and B consisted of 50:50 ACN:$H_2O$ with 0.2% v/v formic acid and 10 mM ammonium formate, and 95:5 ACN:$H_2O$ with 0.2% v/v formic acid and 10 mM ammonium formate, respectively. Gradient elution was carried out with 100% mobile phase B until 2 min followed by a linear gradient to 0% B at 12 mins, keeping 0% B up until 15 mins, thereafter returned to 100% B until in 20 mins total run time. The MS instrument was calibrated using a range of sodium formate clusters introduced by 10 μL loop-injection prior to the chromatographic run. The mass calibrant solution consisted of 3 parts of 1 M NaOH to 97 parts of 50:50 water:isopropanol with 0.2% formic acid. The observed mass and isotope pattern perfectly matched the corresponding theoretical values as calculated from the expected elemental formula. Most of the target compounds were detected as $[M+H]^+$ and $[M+Na]^+$ ions. Data processing was performed using the Data Analysis software version 4.3 (Bruker Daltonik GmbH, Bremen, Germany). Quantification was carried out using the peak area in the extracted ion chromatogram (EIC) of the sum of the protonated and sodiated ion of the target compound. The calibration results are shown in Table 9 below.

TABLE 9

| Ingredient | Time injected (min) | Calibration range (μg/mL) | R-squared |
|---|---|---|---|
| Thymol | 0.8 | 0-9 | 0.98 |
| Xylitol | 2.5 | 0-10 | 0.97 |
| Sorbitan monolaurate | 0.8 | 0-3 | 0.99 |
| Glycerol | 4.0 | 0-9 | 0.95 |
| Eucalyptol | 0.8 | 0-9 | 0.97 |

The calibration range was in the region of the calibration curve which gave a good linear calibration, and therefore excludes points outside this range. Menthol, potassium nitrate and sodium fluoride were not detected by this method.

Using the mass spectrometry data obtained, it is possible evaluate the release profiles of the active ingredients present in the sports-gel style mouthwash under simulated mastication conditions. A comparison of the individual release rate profiles for each active ingredient demonstrates the differential release profile of the mouthwash composition.

Figure 1:
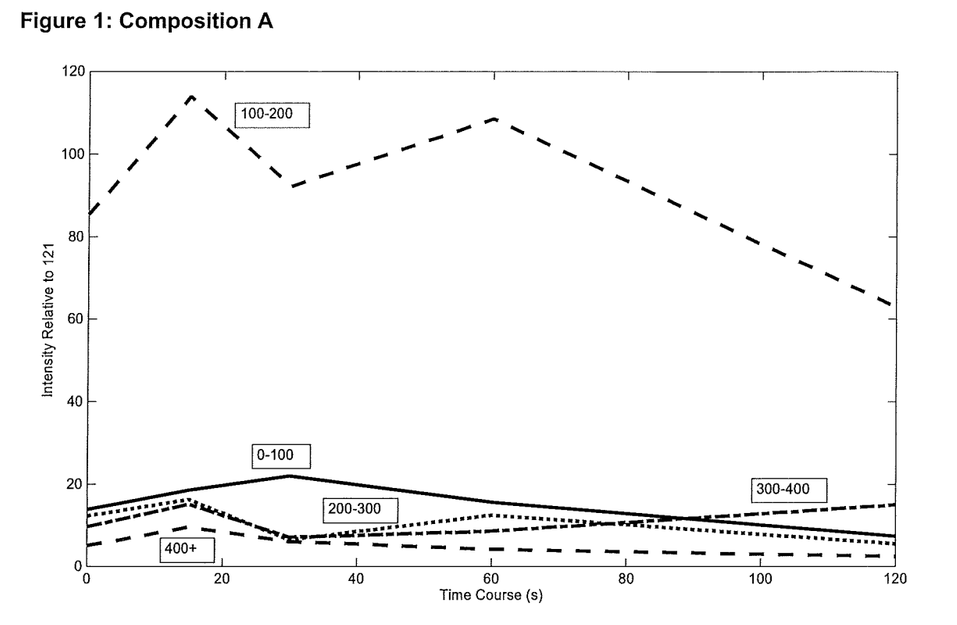
FIGS. 1 to 6 are electrospray ionization (ESI) profiles showing the release of molecules from mouthwash compositions in accordance with embodiments of the invention.
Figure 2:
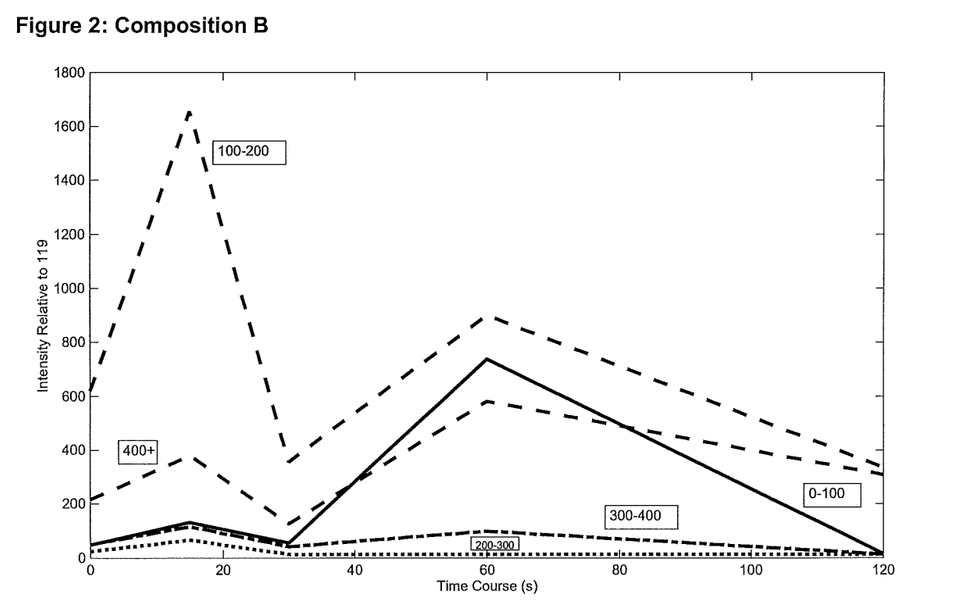
Figure 3:
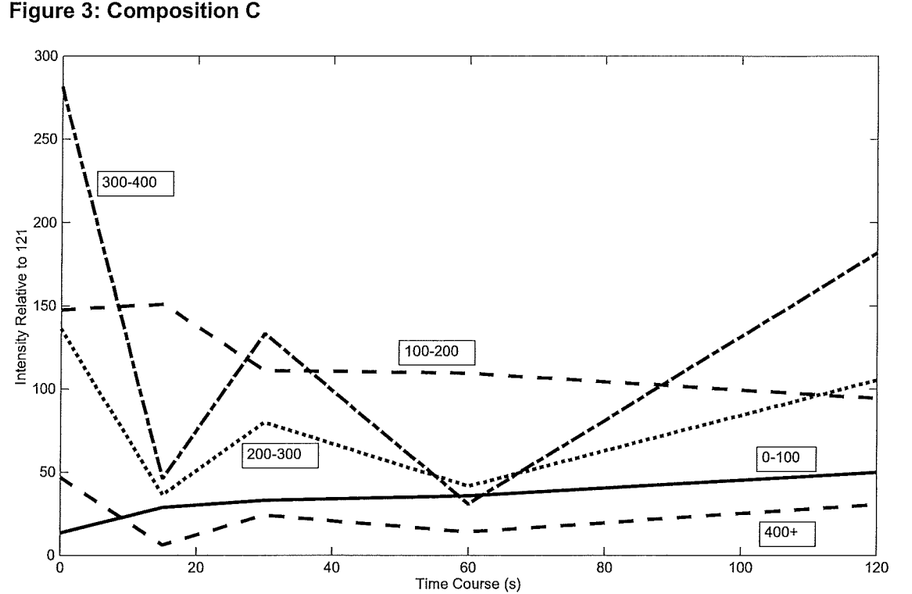
Figure 4:
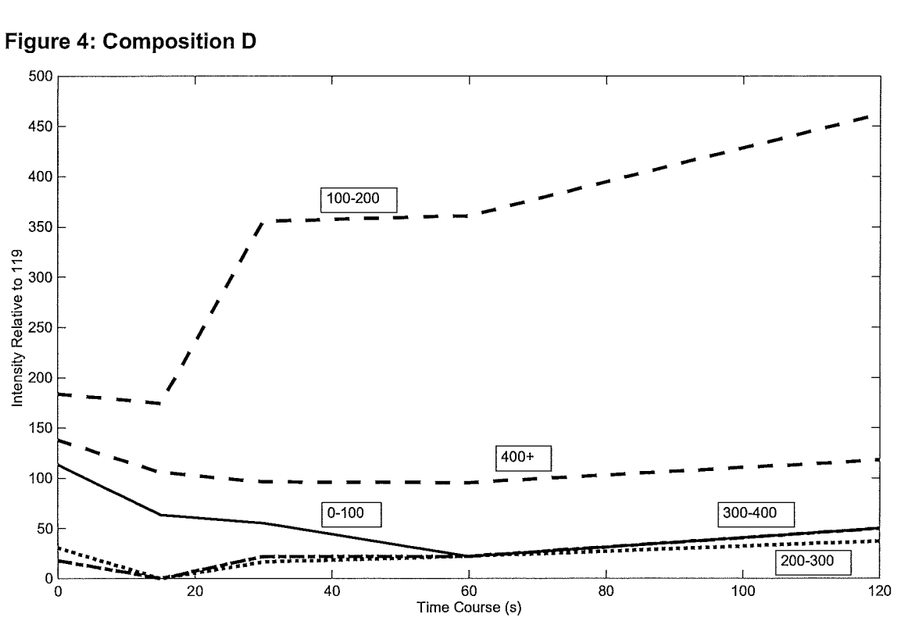
Figure 5:
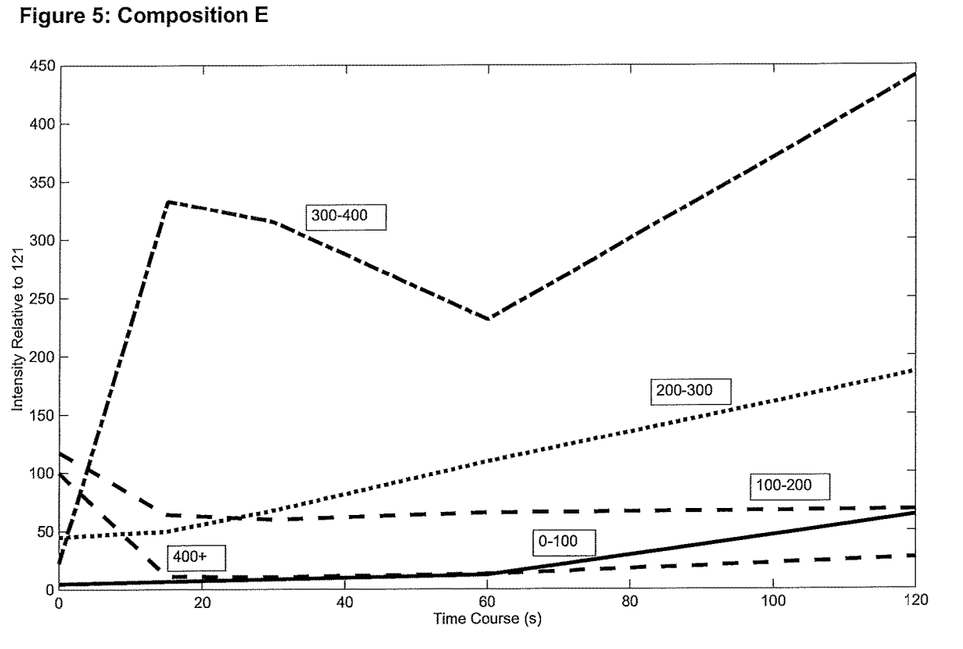
Figure 6:
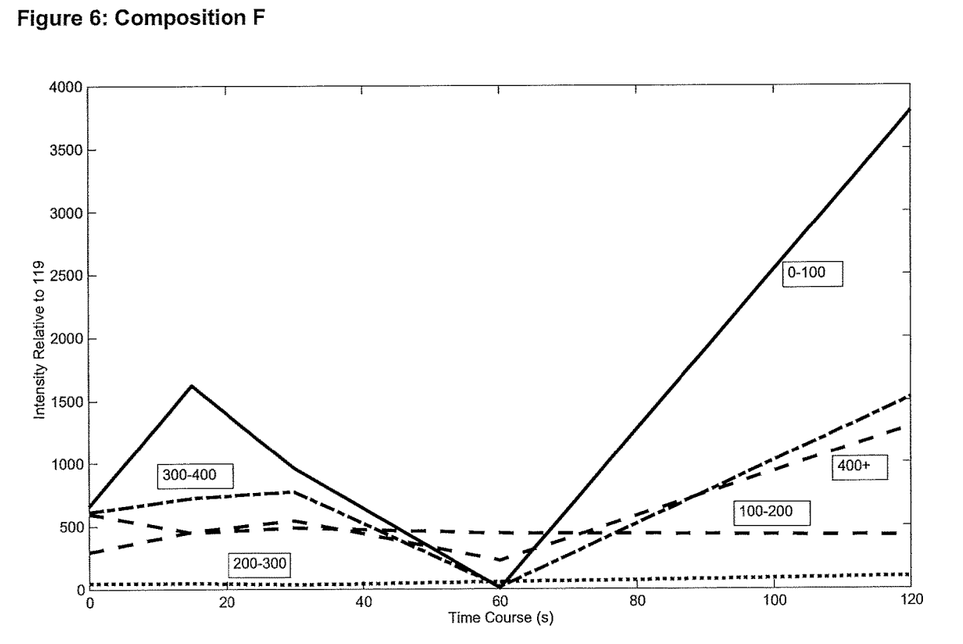
Figure 7:
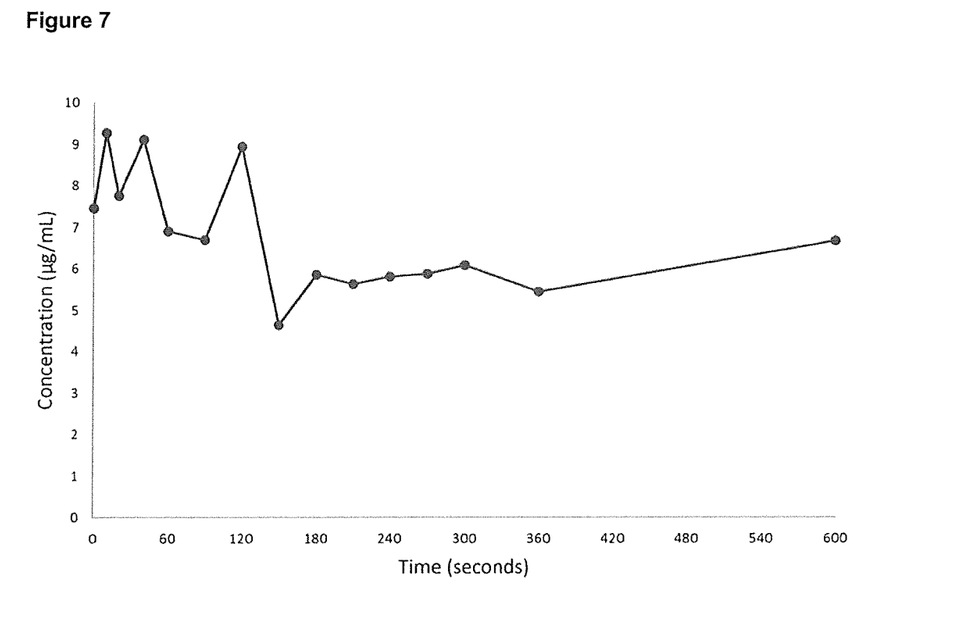
FIG. 7 is a plot showing the release profile of glycerol from a sports-gel style mouthwash prepared according to protocol 1B.

FIG. 7 is a plot showing the release profile of glycerol from a sports-gel style mouthwash prepared according to protocol 1B. Referring to FIG. 7, it can be seen that glycerol immediately releases into the surrounding solution and reaches its effective concentration within seconds to provide a sweet initial flavour in the mouth of the consumer. This will mask the taste of subsequent less pleasant tasting active ingredients. This fast release is due to the low affinity of glycerol for the two gels present in the mouthwash composition, in addition to the high concentration of glycerol in the composition.

Figure 8:
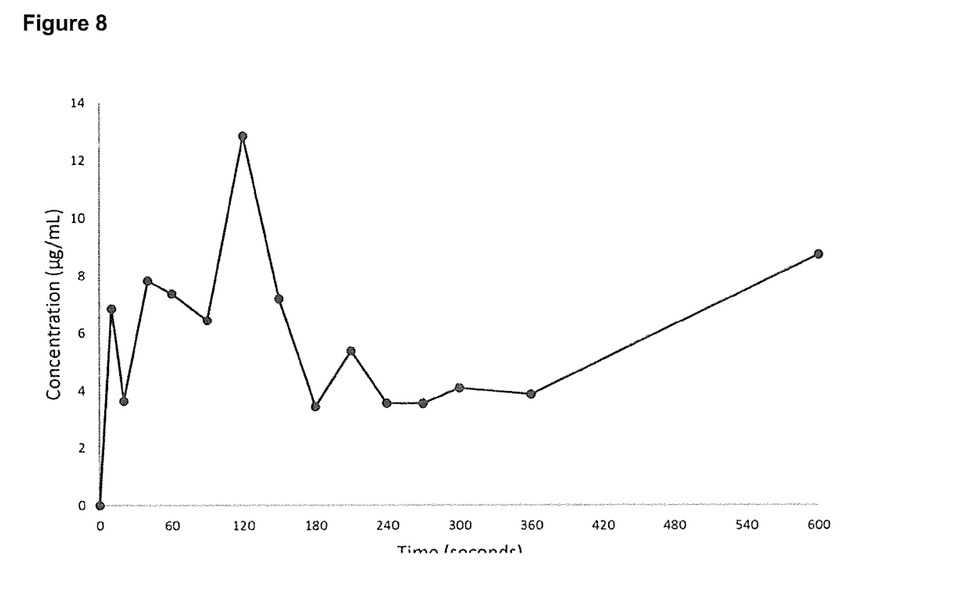
FIG. 8 is a plot showing the release profile of sorbitan monolaurate from a sports-gel style mouthwash prepared according to protocol 1B.

FIG. 8 is a plot showing the release profile of sorbitan monolaurate, which acts as a surfactant, from a sports-gel style mouthwash prepared according to protocol 1B. Referring to FIG. 8, it can be seen that a fast release of sorbitan monolaurate occurs. The sorbitan monolaurate must be released quickly because it plays a crucial role in allowing the composition to form a film upon contact with the buccal surface. This film increases the residence time of the other active ingredients present in the mouthwash composition on the buccal surface and can also help to retain the active ingredients on the buccal surface after the majority of the composition has been swallowed. It is therefore important that the sorbitan monolaurate surfactant is released early during mastication to enable the film to be formed as soon as possible.

Figure 9:
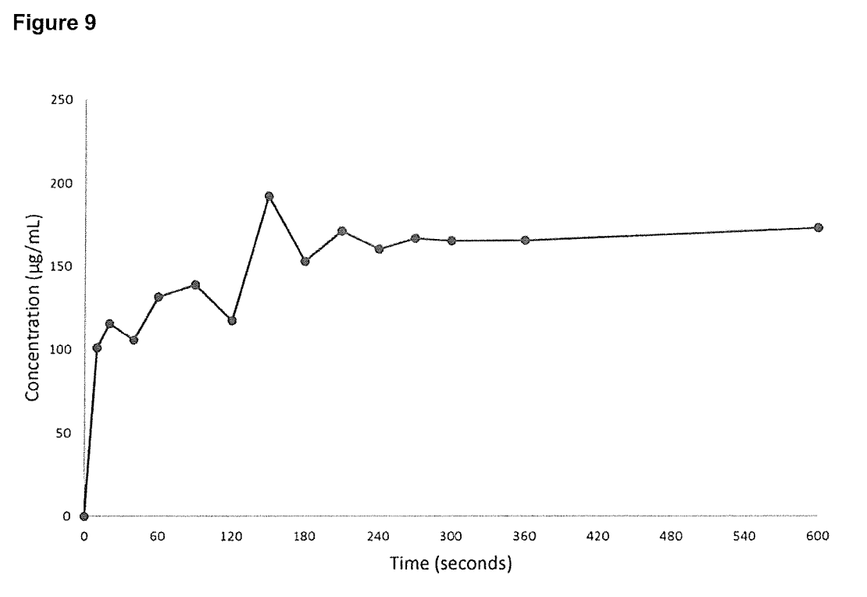
FIG. 9 is a plot showing the release profile of xylitol from a sports-gel style mouthwash prepared according to protocol 1B.

FIG. 9 is a plot showing the release profile of xylitol, which acts as a sweetening agent, from a sports-gel style mouthwash prepared according to protocol 1B. Referring to FIG. 9, it can be seen that xylitol is released quickly from the mouthwash composition. This fast release can be explained by the low affinity of xylitol, which is negatively charged in aqueous medium, for the gelling agent Gellan type F, which is a hydrophobic polymer. The fast release of xylitol allows any unpleasant or bitter flavours originating from the potassium nitrate or menthol also present to be masked.

Figure 10:
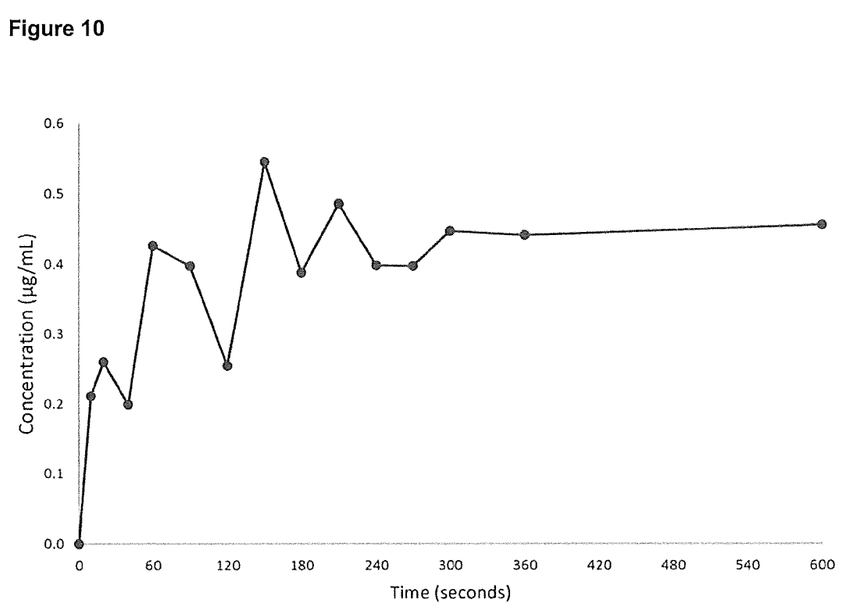
FIG. 10 is a plot showing the release profile of eucalyptol from a sports-gel style mouthwash prepared according to protocol 1B.

FIG. 10 is a plot showing the release profile of eucalyptol, which acts as a flavouring, from a sports-gel style mouthwash prepared according to protocol 1B. In this particular mouthwash composition, eucalyptol is mixed with the gelling agent Gellan LT100, for which it has a relatively high affinity. Referring to FIG. 10, it can be seen that eucalyptol reaches its maximum concentration significantly later than, for example, the glycerol or sorbitan monolaurate. This slower release of eucalyptol is desirable because it allows the flavour to persist over extended periods of mastication.

Figure 11:
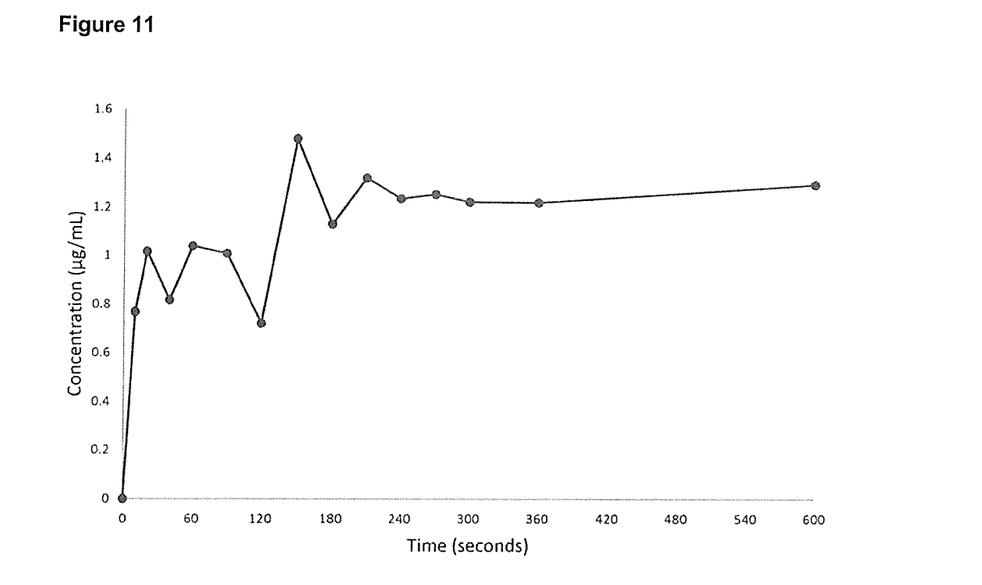
FIG. 11 is a plot showing the release profile of thymol from a sports-gel style mouthwash prepared according to protocol 1B.

FIG. 11 is a plot showing the release profile of thymol, which acts as a preservative and antiseptic, from a sports-gel style mouthwash prepared according to protocol 1B. Referring to FIG. 11, it can be seen that thymol also reaches its maximum concentration at a later stage of mastication and therefore that a more gradual release of preservative occurs over time.

Figure 12:
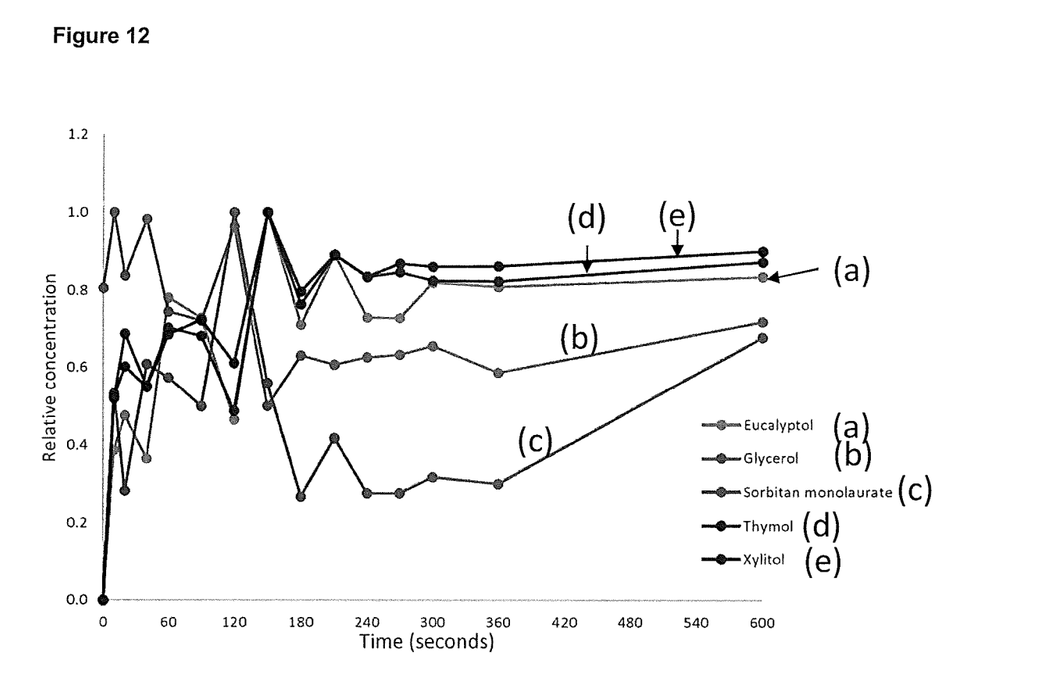
FIG. 12 is a plot showing the relative release profiles of glycerol, sorbitan monolaurate, xylitol, eucalyptol and thymol from a sports-gel style mouthwash prepared according to protocol 1B.

FIG. 12 is a plot showing the relative release profiles of glycerol, sorbitan monolaurate, xylitol, eucalyptol and thymol from a sports-gel style mouthwash prepared according to protocol 1B.

A comparison of each of the individual release profiles allows the differential and sequential release of effective amounts of the active ingredients to be observed over time. Thus FIG. 12 shows each of the plots of FIGS. 7-11 on a single plot after peak normalisation. Referring to FIG. 12, it can be seen that the sweetener glycerol is released immediately upon commencing mastication to provide an initial sweet taste. The surfactant sorbitan monolaurate is the next active ingredient to reach an effective concentration, thereby allowing film formation on the buccal surface to occur at an early stage. The sweetener xylitol then the flavouring eucalyptol can be seen to follow the release of the surfactant. Finally, the preservative and antiseptic thymol is the last active ingredient to release. The results therefore show that upon mastication, the mouthwash composition sequentially releases an effective amount of each of the active ingredients over a period of time.

The invention claimed is:

1. An edible mouthwash composition comprising a heterogeneous gel comprising two or more gels which are blended together but not homogenized, and two or more active ingredients:
   wherein said heterogeneous gel comprises: (i) a first gel comprising a surfactant, a first gelling agent and one or more active ingredients; and (ii) a second gel comprising a second gelling agent and one or more active ingredients,
   wherein the first and second gelling agents are selected from xanthan gum, gellan gum, gum arabic, guar gum, locust bean gum, methylcellulose, carboxymethyl cellulose, gelatin, carrageenan, agar and pectin;
   one of said active ingredients is xylitol;
   the other of said active ingredient(s) is selected from the group consisting of flavourants, antiseptics, antibiotics, anticaries agents, tartar control agents, oral cleaning agents, abrasive agents, desensitizing agents, sweetening agents, medicaments, pro-drugs, activating agents for activating pro-drugs, pH-buffering agents, cooling agents, herbal agents, vitamins and combinations thereof,
   the composition has a viscosity of from 1000 to 2000 c.p. at 20° C.; and
   the composition provides differential release of the active ingredients over a period of time.

2. The mouthwash composition according to claim 1, wherein said composition sequentially releases an effective amount of said surfactant and an effective amount of at least one of said one or more active ingredients over a period of time.

3. The mouthwash composition according to claim 1, wherein the composition forms a film upon contact with a buccal surface.

4. The mouthwash composition according to claim 1, wherein the heterogeneous gel comprises methylcellulose and xanthan gum, or wherein the heterogeneous gel comprises gellan gum.

5. The mouthwash composition according to claim 1, wherein said composition comprises a sweetening agent.

6. The mouthwash composition according to claim 1, wherein the heterogeneous gel contains a pro-drug and an activating agent for activating the pro-drug.

7. The mouthwash composition according to claim 1, wherein the composition is in the form of a jelly or the composition is the form of a chewable sweet having a mass of from 5 to 15 g.

8. A method of preparing a mouthwash composition in the form of a gel as claimed in claim 1, the method comprising:
   providing a first component;
   providing a second component; and
   mixing the first and second components together to provide a heterogeneous mixture,
   wherein the first and second components each comprises at least one active ingredient, and
   the composition comprises two or more active ingredients.

9. The method according to claim 8, wherein the first and/or second component is in the form of a gel prior to mixing.

10. The method according to claim 8, wherein the first and/or second component is in the form of a solution comprising a gelling agent.

11. The method of claim 10, further comprising adding a further gelling agent to the heterogeneous mixture prior to allowing the mixture to set.

12. The method according to claim 8, further comprising adding a colouring and/or a flavouring to the heterogeneous mixture.

13. The method according to claim 8, further comprising encapsulating the heterogeneous mixture.

14. A package comprising a single dose or unit of the mouthwash composition as claimed in claim 1.

15. A method of cleaning teeth and/or freshening breath in a subject comprising administering the mouthwash composition as claimed in claim 1.

16. The method according to claim 9, wherein providing the first and/or second components comprises dissolving a gelling agent in water with heating to form a solution and allowing the solution to cool so as to form a gel prior to mixing.

17. The method according to claim 10, wherein the method comprises a further step of allowing the heterogeneous mixture to set.

18. The method according to claim 11, further comprises dispensing the heterogeneous mixture into a mould prior to allowing the mixture to set.

19. The method according to claim 13, wherein encapsulating the heterogeneous mixture comprises injecting the heterogeneous mixture into a hollow shell.

20. The mouthwash composition according to claim 1, wherein said composition further comprises sodium fluoride and a flavorant selected from peppermint oil, menthol, eucalyptol, and thymol.

* * * * *